US012751931B2

(12) United States Patent
Svendsen et al.

(10) Patent No.: US 12,751,931 B2
(45) Date of Patent: Oct. 6, 2026

(54) PREVENTION OF VIRAL TRANSMISSION THROUGH FEED

(71) Applicant: DSM IP Assets B.V., Heerlen (NL)

(72) Inventors: Ole-Lund Svendsen, Kaiseraugst (CH); Jon Bergstrom, Kaiseraugst (CH)

(73) Assignee: DSM IP ASSETS B.V., Maastricht (NL)

( * ) Notice: Subject to any disclaimer, the term of this patent is extended or adjusted under 35 U.S.C. 154(b) by 675 days.

(21) Appl. No.: 17/801,098

(22) PCT Filed: Feb. 19, 2021

(86) PCT No.: PCT/EP2021/054090
§ 371 (c)(1),
(2) Date: Aug. 19, 2022

(87) PCT Pub. No.: WO2021/165436
PCT Pub. Date: Aug. 26, 2021

(65) Prior Publication Data

US 2023/0189843 A1 Jun. 22, 2023

(30) Foreign Application Priority Data

Feb. 20, 2020 (EP) .................................... 20158422

(51) Int. Cl.

| | |
|---|---|
| ***A61K 31/05*** | (2006.01) |
| ***A23K 20/111*** | (2016.01) |
| ***A23K 50/30*** | (2016.01) |
| ***A61K 31/085*** | (2006.01) |
| ***A61K 31/192*** | (2006.01) |
| ***A61P 11/00*** | (2006.01) |

(52) U.S. Cl.
CPC ............ *A61K 31/05* (2013.01); *A23K 20/111* (2016.05); *A23K 50/30* (2016.05); *A61K 31/085* (2013.01); *A61K 31/192* (2013.01); *A61P 11/00* (2018.01)

(58) Field of Classification Search
CPC ...... A23K 20/111; A23K 50/30; A23K 30/00; A61K 31/05; A61K 31/085; A61K 31/192; A61P 11/00
See application file for complete search history.

(56) References Cited

U.S. PATENT DOCUMENTS 8,980,335 B2 3/2015 Frehner et al.

FOREIGN PATENT DOCUMENTS

| | | |
|---|---|---|
| CN | 101331915 | 12/2008 |
| EP | 2042041 A2 | 4/2009 |
| WO | 2011/017367 | 2/2011 |
| WO | 2016/081716 | 5/2016 |

OTHER PUBLICATIONS

Abudabos et al. Effects of the Essential Oil Blend CRINA® Poultry in Feed on Broiler Performance and Gut Microbiology, Italian Journal of Animal Science, 12:4, e83, 2013. (Year: 2013).*
Crina® Poultry Plus. EFSA Journal 2014; 12(11):3896. (Year: 2014).*
Gebhardt et al. Kansas Agricultural Experiment Station Research Reports 2.8 (2016): 4. (Year: 2016).*
Baudoux, Dominque, "Antiviral and Antimicrobial effects of essential oil", *Perfumes, Essences and Cosmetics*, No. 5, pp. 40-45 (English Abstract).
International Search Report dated May 17, 2021, for PCT/EP2021/054090, 3 pp.
Written Opinion of the ISA dated May 17, 2021, for PCT/EP2021/054090, 7 pp.
H. Zhai et al., "The effects of benzoic acid and essential oils on growth performance, nutrient digestibility, and colonic microbiota in nursery pigs", Animal Feed Science and Technology, vol. 262, Jan. 22, 2020, 20 pp.
Jordan T. Gebhardt et al., "Determining the impact of commercial feed additives as potential porcine epidemic diarrhea virus mitigation strategies as determined by polymerase chain reaction analysis and bioassay", Translational Animal Science, vol. 3, No. 1, Aug. 20, 2018, 10 pp.
Unknown, "Research on Viral Transmission in Feedstuffs Yields New Information", Swine Health Information Center (SHIC), Newsletter, May 7, 2019, Ames, Iowa, 2 pp., at URL: https://www.swinehealth.org/research-on-viral-transmission-in-feedstuffs-yields-new-information/.
Stephen A. Bustin et al., "Real-time reverse transcription PCR (qRT-PCR) and its potential use in clinical diagnosis", Clinical Science, vol. 109, 2005, printed in Great Britain, pp. 365-379 (15 pp.).
Scott Dee et al., "An evaluation of contaminated complete feed as a vehicle for porcine epidemic diarrhea virus infection of naïve pigs following consumption via natural feeding behavior: proof of concept", BMC Veterinary Research, vol. 10, No. 176, 2014, 9 pp.
M.P. Trudeau et al., "Survival and mitigation strageies of porcine epidemic diarrhea virus (PEDV) in complete feed", American Dairy Science Association , Midwest American Society of Animal Science, Mar. 16, 2015, https://asas.confex.com/asas/mw15/webprogram/Paper11652.html.
Ministry of Science and Technology, Substantive Examination Report, Vietnam Appln. No. 1-2022-05402, Mar. 18, 2026.

* cited by examiner

*Primary Examiner* — Erik Kashnikow
*Assistant Examiner* — Janice Y Silverman
(74) *Attorney, Agent, or Firm* — NIXON & VANDERHYE P.C.

(57) ABSTRACT

The present invention relates to a computer-implemented method of determining the need of adding a mitigant to feed for inactivating viruses that might be present in said feed. The preferred mitigant is a mixture comprising benzoic acid flakes and a powder that comprises eugenol and thymol. Said mixture inactivates viruses quickly, even when added in low concentration only. This applies in particular (but not only) to porcine epidemic diarrhea vims (PEDV). The animal feed, by way of the invention, is thus rendered to be substantially free of harmful viral RNA.

10 Claims, 1 Drawing Sheet

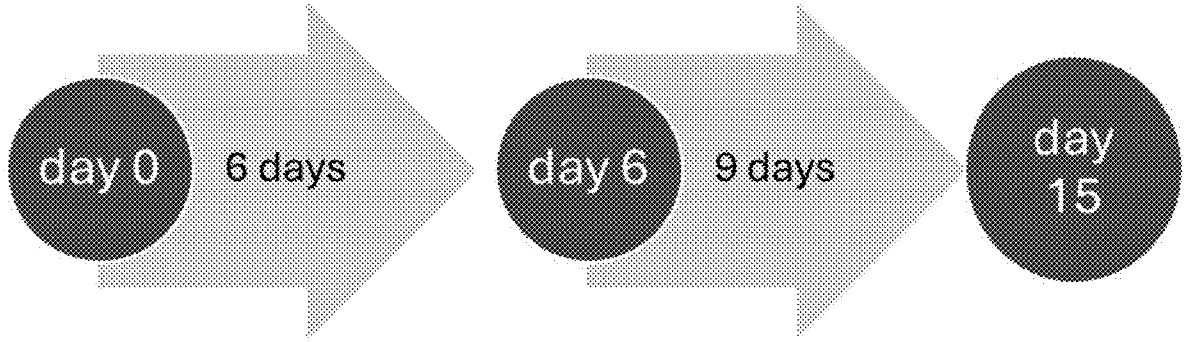
day 0
6 days
day 6
9 days
day
15

PREVENTION OF VIRAL TRANSMISSION THROUGH FEED

CROSS-REFERENCE TO RELATED APPLICATIONS

This application is the U.S. national phase of International Application No. PCT/EP2021/054090 filed Feb. 19, 2021, which designated the U.S. and claims priority to EP 20158422.4 filed Feb. 20, 2020, the entire contents of each of which are hereby incorporated by reference.

TECHNICAL FIELD

The present invention deals with the threat of viral pathogens in feed.

BACKGROUND OF THE INVENTION

Feed and feed ingredients have been proposed to be contributing factors to the introduction of porcine epidemic diarrhea virus (PEDV) in commercial swine herds. This route of infection has been proven possible in experimental settings (Dee et al. "An evaluation of contaminated complete feed as a vehicle for porcine epidemic diarrhea virus infection of naïve pigs following consumption via natural feeding behavior: proof of concept" BMC Veterinary Research, 2014; 10:176).

The Swine Health Information Center (SHIC), the National Pork Board, the National Pork Producers Council and the American Association of Swine Veterinarians suggest adding more holding time to assure viral degradation in feed. For conventional soybean meal, they recommend 143 days holding time at 4° C. for 99.99% degradation (Swine Health Information Center, "Research on viral transmission in feedstuffs yields, new information", release on May 7, 2019).

WO 2011/017367 discloses antimicrobial compositions containing buffered propionic or acetic acid mixed with pelargonic acid. The examples of WO 2016/081716 disclose animal feed comprising from about 0.01 weight-% to about 5 weight-% of a combination of medium chain fatty acid and an essential oil mix. Gebhardt et al. assessed 0.5% inclusion of a benzoic acid, 0.02% inclusion of an essential oil product and a combination thereof in spray-dried porcine plasma and a swine gestation diet (Gebhardt et al., "Determining the impact of commercial feed additives as potential porcine epidemic diarrhea virus mitigation strategies as determined by polymerase chain reaction analysis and bioassay", Translational Animal Science, 1 Jan. 2019, (1):134-142; citation from the introduction).

Guardian® is a commercially available product which is claimed to combat viral pathogens in feed and/or ingredients. The supplier of this product recommends an inclusion rate of 4 kg per metric ton of feed corresponding to 0.4 weight-%. If a farmer follows this recommendation, cost for feed increases by approximately 19.8 US$ per metric ton of feed. Because the meat industry is very cost sensitive, additional cost of 19.8 US$ per metric ton may be prohibitive.

There is a need for a solution that is less expensive and/or more effective.

SUMMARY OF THE INVENTION

When combatting viral pathogens in feed, one would assume that a substantial increase in mixture concentration and/or increase in time would increase effectiveness of the treatment. This is not necessarily the case if a mixture of benzoic acid, eugenol and thymol is used.

For mitigation of Porcine Epidemic Diarrhea virus (PEDV), Gebhardt et al. teach to use 0.5% inclusion of a benzoic acid and 0.02% inclusion of an essential oil product. Surprisingly, a lower concentration is enough if the essential oil that is used in combination with benzoic acid comprises eugenol and thymol. One embodiment of the invention relates to a method of inhibiting porcine epidemic diarrhea virus in animal feed, wherein benzoic acid, eugenol and thymol are added to animal feed in a total amount of less than 0.5 weight-%, based on the total weight of the feed. A preferred embodiment of the invention relates to a method of inhibiting porcine epidemic diarrhea virus in animal feed, wherein benzoic acid is added to the animal feed in an amount from 0.25 to 0.475 weight-%, based on the total weight of the feed, and/or wherein a powder comprising eugenol and thymol is added in an amount from 0.010 to 0.019 weight-% of, based on the total weight of the feed. In comparison with eugenol and thymol, commercially available benzoic acid flakes are relatively cheap. Therefore, the claimed solution is less expensive than the solution of the prior art comprised of higher levels of only the essential oils.

The same low concentrations are also effective for mitigation of Porcine Reproductive and Respiratory Syndrome virus (PRRSV) and Seneca Virus A (SVA). One embodiment of the invention relates to a method of inhibiting the PRRS virus and/or SVA in animal feed, wherein benzoic acid, eugenol and thymol are added to animal feed in a total amount of less than 0.5 weight-%, based on the total weight of the feed. A preferred embodiment relates to a method of inhibiting PRRS virus and/or SVA in animal feed, wherein benzoic acid is added to the animal feed in an amount from 0.25 to 0.475 weight-%, based on the total weight of the feed, and/or wherein a powder comprising eugenol and thymol is added in an amount from 0.010 to 0.019 weight-% of, based on the total weight of the feed.

Whereas the addition of benzoic acid, eugenol and thymol to feed in a total amount of less than 0.5 weight-%, based on the total weight of the feed, is effective for mitigation of all three viruses (i.e. PRRSV, SVA and PEDV), the mixture acts at this concentration quicker on PEDV than on PRRSV and SVA. Mitigation speed is highly beneficial as it allows for a reduction of the holding time recommended by the Swine Health Information Center (SHIC) and others. A preferred embodiment of the invention relates to the use of a mixture comprising benzoic acid, eugenol and thymol for reducing the holding time that needs to be applied to allow for degradation of porcine epidemic diarrhea virus in animal feed.

PCR (polymerase chain reaction) testing has proven to be sensitive for PRRSV and PEDV. One embodiment of the invention relates to a computer-implemented method of preparing feed, said method comprising the steps:

a) providing a sample of at least one feed ingredient and determining the value for Ct by real-time quantitative reverse transcriptase polymerase chain reaction for at least one predetermined virus;
b) providing a model which defines Ct values that are in range in case a feed ingredient is contaminated with a virus;
c) using said model to determine if a mitigant for inactivating viruses needs to be added to feed that comprises the feed ingredient of step a).

Ct values represent the cycle fractions where the instrument can first detect fluorescence derived from the amplification reaction (threshold cycle) as further explained for example in Bustin, S. A., & Mueller, R. (2005), "Real-time reverse transcription PCR (qRT-PCR) and its potential use in clinical diagnosis" Clinical Science, 109(4), 365-379. If a Ct value is "in range", the number of viruses is high enough to be easily detected by real-time quantitative reverse transcriptase polymerase chain reaction. If a Ct value is "out of range", the number of viruses is zero or so low that the virus does not do any harm. In respect of the herein discussed viruses, Ct values of ≥38 are an indication for the absence of the respective virus. Ct values of ≤37 are an indication for the presence of the respective virus.

DETAILED DESCRIPTION OF THE INVENTION

The present invention relates inter alia to a computer-implemented method of determining the need of adding a mitigant to feed for inactivating viruses that might be present in a feed ingredient intended for preparing said feed. The preferred mitigant is a mixture comprising benzoic acid flakes and a powder that comprises eugenol and thymol. Said mixture inactivates viruses quickly even when added to feed in low concentration. This applies, in particular, but not only to porcine epidemic diarrhea virus (PEDV). The animal feed, by way of the invention, is thus rendered to be free of harmful viral RNA.

Animal Feed of the Invention

The animal feed of the present invention may be preferably feed for birds, fish or mammals. In a preferred embodiment of the invention, the animal feed is pig feed. Typical ingredients of pig feed are ground corn or other grains, with soybean or other plant-sourced protein products.

The animal feed of the invention comprises benzoic acid, eugenol and thymol so that it is preferably free of viral RNA (ribonucleic acid). Preferably, "free of viral RNA" means that the respective Ct value is 38 or above. More preferably, it means that no viral RNA can be detected by real-time quantitative reverse transcriptase polymerase chain reaction.

The present invention relates preferably to a virus selected from the group consisting of porcine epidemic diarrhea virus, porcine reproductive and respiratory syndrome virus and seneca virus A. As used in the context of the present invention, "porcine epidemic diarrhea virus", PED virus and PEDV are synonyms. As used in the context of the present invention, porcine reproductive and respiratory syndrome virus, PRRS virus and PRRSV are synonyms. As used in the context of the present invention, seneca virus A and SVA are synonyms. Thus, "free of viral RNA" means preferably that no viral RNA from PEDV, PRRS and/or SVA can be detected by real-time quantitative reverse transcriptase polymerase chain reaction. When there are multiple strains of a virus, all strains are included. In case of PRRSV, the preferred strain is PRRSV 174. In some U.S. pig producing areas, this strain of PRRSV is rather common; it is recognized as being highly virulent and severe.

In some embodiments, the term "viral RNA" refers preferably not to viral RNA from seneca virus A as PCR may give false positive results in case of SVA. In this embodiment, "free of viral RNA" preferably means that no viral RNA from PEDV and PRRS can be detected by real-time quantitative reverse transcriptase polymerase chain reaction.

The animal feed of the invention comprises benzoic acid, eugenol and thymol in a total amount of preferably less than 0.5 weight-%, more preferably less than 0.4 weight-%, based on the total weight of the feed. In the most preferred embodiment, the animal feed of the invention comprises benzoic acid flakes and a powder that comprises eugenol and thymol, wherein the total amount of benzoic acid flakes and said powder is 0.312 weight-%, based on the total weight of the feed.

In another embodiment, the animal feed of the invention comprises:

0.25 to 0.475 weight-%, preferably 0.25 to 0.4 weight-% and most preferably 0.25 to 0.39 weight-%, benzoic acid, based on the total weight of the feed, and from 0.010 to 0.019 weight-% of a powder, based on the total weight of the feed, wherein said powder comprises eugenol and thymol, and wherein the weight ratio between benzoic acid and eugenol is preferably at least 500:1, more preferably at least 833:1 and is preferably at most 2500:1, and/or wherein the weight ratio between benzoic acid and thymol is preferably at least 250:1, more preferably at least 333:1 and is preferably at most 500:1.

In one embodiment, the animal feed of the invention comprises benzoic acid and a powder, wherein said powder comprises eugenol and thymol and preferably at least one auxiliary compound. Such powder is commercially available at DSM® Nutritional Products (Switzerland). In a preferred embodiment, the animal feed of the invention comprises benzoic acid flakes and a powder, wherein said powder comprises eugenol, thymol and at least one auxiliary compound, and wherein said powder comprises preferably from 10 weight-% to 60 weight-%, more preferably from 10 weight-% to 53 weight-%, and most preferably from 10 weight-% to 30 weight-% auxiliary compounds, based on the total weight of the powder. Eugenol and thymol are preferably in physical contact with the feed ingredients and any viruses that may be present. Therefore, the powder which comprises eugenol, thymol and the at least one auxiliary compound is preferably not coated. Therefore, the powder which comprises eugenol, thymol and the at least one auxiliary compound comprises preferably less than 5 weight-% of fully hydrogenated fat, partially hydrogenated fat and/or non-hydrogenated fat. In these embodiments, 0.25 to 0.475 weight-% benzoic acid, based on the total weight of the feed, is preferably added. Such powder is preferably added in a total amount from 0.010 to 0.019 weight-%, based on the total weight of the feed. Benzoic acid flakes are commercially available at DSM® Nutritional Products (Switzerland).

METHOD OF THE INVENTION

The present invention also relates to a method of inhibiting viruses in animal feed, wherein benzoic acid (preferably benzoic acid flakes) and a powder comprising eugenol and thymol is added to animal feed, preferably in an total amount of less than 0.5 weight-%, more preferably in an total amount of less than 0.48 weight-%, based on the total weight of the feed. This method is suitable for inhibiting any kinds of potentially harmful viruses. In a preferred embodiment, the present invention relates to a method of inhibiting porcine epidemic diarrhea virus, of inhibiting porcine reproductive and respiratory syndrome virus or of inhibiting non-enveloped RNA viruses such seneca virus A. In the most preferred embodiment, the present invention relates to a method of inhibiting porcine epidemic diarrhea virus. In said methods, 0.25 to 0.475 weight-% benzoic acid, based on the total weight of the feed, are preferably added to the feed, whereas a powder comprising eugenol and thymol is preferably added in an amount from 0.010 to 0.019 weight-%, based on the total weight of the feed.

In the animal feed, the combination of benzoic acid, eugenol and thymol is preferably in physical contact with the feed ingredients and any viruses that may be present. Therefore, the powder comprising eugenol and thymol should preferably not be lipid coated. The powder comprising eugenol and thymol are preferably not prills. The powder comprising eugenol and thymol as used in the method of the invention comprises preferably less than 5 weight-%, more preferably less than 4 weight-% and even preferably more preferably less than 3 weight-% of fully hydrogenated, partially hydrogenated and/or non-hydrogenated fat, based on the total weight of the powder. Other auxiliary compounds such as fillers and glidants are acceptable. The powder comprising eugenol and thymol as used in the method of the invention comprises preferably from 1 weight-% to 50 weight-%, more preferably from 5 weight-% to 40 weight-% and most preferably from 10 weight-% to 30 weight-% auxiliary compounds, based on the total weight of the powder.

USE OF THE INVENTION

Most viruses have a half-life. Thereby, half-life is the time taken for half of a number of viruses to die off naturally. Because viral survivability in feed is limited, holding times are one manner to mitigate viral risk. Recently, the Swine Health Information Center (SHIC) has posted guidelines on its website for calculating suitable holding times.

In the context of the present invention, the term "holding time" refers to a period of time feed or feed ingredients are stored prior to being fed to the animals. Typical holding times are days or even weeks.

A mixture comprising benzoic acid, eugenol and thymol inactivates RNA viruses in feed and feed ingredients. As a result, holding times are rendered moot or are at least substantially shortened. The present invention relates to the use of a mixture comprising benzoic acid, eugenol and thymol for reducing the holding time that needs to be applied to allow for viral degradation in animal feed. Thereby, holding time is reduced preferably to less than 7 days, more preferably to less than 6 days, even more preferably to less than 5 days and most preferably to less than 3 days. In a preferred embodiment, viral RNA from porcine epidemic diarrhea virus, from porcine reproductive and respiratory syndrome virus and/or from seneca virus A is degraded.

Thus, the invention relates to the use of a mixture comprising benzoic acid, eugenol and thymol for reducing the holding time that needs to be applied to allow for degradation of viral RNA from porcine epidemic diarrhea virus, from porcine reproductive and respiratory syndrome virus and/or from seneca virus A in animal feed, wherein the holding time is reduced preferably to less than 7 days, more preferably to less than 6 days, even more preferably to less than 5 days and most preferably to less than 3 days. The most preferred embodiment relates to the use of a mixture comprising benzoic acid, eugenol and thymol for reducing the holding time that needs to be applied to allow for degradation of viral RNA from porcine epidemic diarrhea virus in animal feed, wherein the holding time is reduced to preferably less than 3 days.

In mixtures relating to these embodiments, the weight ratio benzoic acid and eugenol is preferably at least 500:1, more preferably at least 833:1 and is preferably at most 2500:1, wherein the weight ratio between benzoic acid and thymol is preferably at least 250:1, more preferably at least 333:1 and is preferably at most 500:1.

Computer-Implemented Method of the Invention

Typically, feed is prepared by feed mills. To do so, feed mills buy primary feed ingredients (such as ground corn and soybean meal) and other feed ingredients (such as minerals, vitamins and other feed additives). A feed ingredient that is present in an amount of preferably at least 20 weight-%, based on the total weight of feed, is a "primary feed ingredient".

Commercially available feed ingredients may become contaminated with harmful viruses, especially during their transportation or physical movement. Feed mills must therefore take measures to ensure that the feed that they are selling is free of harmful viruses. One measure is to store feed ingredients and/or feed for several days or weeks (holding time). This measure assumes that there is little or no further risk for contamination during the subsequent, final movement of the feed to where it will be consumed.

The computer-implemented method of the invention allows for a reduction of holding times and/or renders holding times completely moot. In a preferred embodiment, the computer-implemented method of the invention makes sure that mitigants for inactivating viruses are only added if the presence of a harmful virus has been confirmed.

The computer-implemented method of the present invention can be based on various forms of hardware, software, firmware, processors, distributed servers (e.g., as used in cloud computing) or a combination thereof. In one embodiment, the computer-implemented method of the present invention involves the use of communication infrastructure, for example the internet.

The computer-implemented method of the present invention requires the determination of Ct values by real-time quantitative reverse transcriptase polymerase chain reaction. To do so, a PCR apparatus is needed. Therefore, a combination of hardware and software is preferably used when implementing the computer-implemented method of the invention.

The software can be implemented as an application program tangibly embodied on a program storage device, or different portions of the software implemented in the user's computing environment (e.g., as an applet) and on the reviewer's computing environment, where the reviewer may be located at a remote site (e.g., at a service provider's facility).

Ct values determined by real-time quantitative reverse transcriptase polymerase chain reaction are then used in a model which defines Ct values that are in range in case a feed ingredient is contaminated with a virus such as PEDV and PRRSV. In a preferred embodiment, the model of the invention is a decision tree. Decision trees are models that contain conditional control statements. In a particularly preferred embodiment, the method of the invention comprises at least one of the following conditional control statements:

IF Ct value determined for PEDV is 37 or below,
  THEN recommend adding at least one mitigant (preferably a mixture of benzoic acid, eugenol and thymol) to the feed that contains the feed ingredient whose Ct value has been determined 37 or below,
  ELSE recommend to refrain from adding a mitigant for inactivating viruses IF Ct value determined for PRRS is 37 or below,
  THEN recommend adding at least one mitigant (preferably a mixture of benzoic acid, eugenol and thymol) to the feed that contains the feed ingredient whose Ct value has been determined 37 or below,
  ELSE recommend to refrain from adding a mitigant for inactivating viruses IF Ct value determined for a non-enveloped virus such as SVA is 37 or below,
THEN recommend adding at least one mitigant (preferably a mixture of benzoic acid, eugenol and thymol) to the feed that contains the feed ingredient whose Ct value has been determined 37 or below,
ELSE recommend to refrain from adding a mitigant for inactivating viruses Ct values of ≤37 are an indication for the presence of the respective virus, i.e. a mitigant for inactivating viruses should be added in case of Ct values of ≤37. In the most preferred embodiment, the method of the invention comprises or consists of the following conditional control statements:

IF Ct value determined for PEDV is 37 or below,
THEN recommend adding at least one mitigant (preferably a mixture of benzoic acid, eugenol and thymol) to the feed that contains the feed ingredient whose Ct value has been determined 37 or below,
ELSE recommend to refrain from adding a mitigant for inactivating viruses IF Ct value determined for PRRS is 37 or below,
THEN recommend adding at least one mitigant (preferably a mixture of benzoic acid, eugenol and thymol) to the feed that contains the feed ingredient whose Ct value has been determined 37 or below,
ELSE recommend to refrain from adding a mitigant for inactivating viruses In one embodiment, an application program for executing the method of the invention is uploaded to and/or executed by a computer platform which has hardware such as one or more central processing units (CPU), a random access memory (RAM), and input/output (I/O) interface(s). This generally includes at least one computer processor. The computer processors can be processors that are typically found in personal desktop computers, portable computers, mainframes, minicomputers, portable electronic devices (e.g., tablets or smart phones). Various other peripheral devices may be connected to the computer platform such as an additional data storage device and a printing device. One embodiment of the present invention relates to a computer-implemented method of preparing feed, said method comprising the steps:

a) providing a sample of at least one feed ingredient and determining the value for Ct by real-time quantitative reverse transcriptase polymerase chain reaction for at least one predetermined virus;
b) providing a model which defines Ct values that are in range in case a feed ingredient is contaminated with a virus;
c) using said model to determine if a mitigant for inactivating viruses needs to be added to feed that comprises the feed ingredient of step a), wherein said at least one feed ingredient is preferably a primary feed ingredient, and/or wherein said at least one feed ingredient is preferably selected from the group consisting of corn, ground corn, a soybean product, soybean meal, canola meal, wheat and barley, and wherein said mitigant is preferably a mixture comprising benzoic acid, eugenol and thymol, and wherein said mixture is added in an amount of preferably less than 0.5 weight-%, based on the total weight of the feed if the Ct value determined for PEDV and/or PRRS is 37 or below.

Whereas the herein preferred mitigants effectively inactivate non-enveloped viruses such as SVA, said mitigants do not always fully disintegrate the RNA of non-enveloped viruses. In case of inactivated but not fully disintegrated viruses, harmless RNA fractions of non-viable viruses may be left-over. In such cases, PCR testing might provide false positive results and therefore, there is no benefit in determining the respective Ct values in costly and may be time consuming lab test. Thus, one embodiment of the present invention relates to a computer-implemented method of determining the need of adding a mitigant to feed for inactivating viruses that might be present in a feed ingredient intended for preparing said feed, said method comprising:

a) providing a sample of at least one feed ingredient and determining the value for Ct by real-time quantitative reverse transcriptase polymerase chain reaction for at least one predetermined virus;
b) providing a model which defines Ct values that are in range in case a feed ingredient is contaminated with a virus;
c) using said model to determine if a mitigant (e.g. a mixture of benzoic acid, eugenol and thymol) needs to be added to feed that comprises the feed ingredient of step a), wherein the value for Ct is not determined for seneca virus A and wherein the value for Ct is preferably not determined for any non-enveloped virus.

Another embodiment of the present invention relates to a computer-implemented method of preparing feed, said method comprising the steps:

a) providing a sample of at least one feed ingredient and determining the value for Ct by real-time quantitative reverse transcriptase polymerase chain reaction for at least one predetermined virus;
b) providing a model which defines Ct values that are in range in case a feed ingredient is contaminated with a virus;
c) using said model to determine if a mitigant for inactivating viruses needs to be added to feed that comprises the feed ingredient of step a), wherein the value for Ct is not determined for seneca virus A and wherein the value for Ct is preferably not determined for any non-enveloped virus, and wherein steps b) and c) preferably comprise at least one of the following two actions:

Action 1:
IF Ct value determined for PEDV is 37 or below,
THEN add at least one mitigant to the feed than contains the feed ingredient whose Ct value has been determined 37 or below,
ELSE refrain from adding a mitigant for inactivating viruses, Action 2:
IF Ct value determined for PRRS is 37 or below,
THEN add at least one mitigant to the feed than contains the feed ingredient whose Ct value has been determined 37 or below,
ELSE refrain from adding a mitigant for inactivating viruses

EXAMPLES

Example 1

In example 1, RNA viruses were introduced in a controlled manner into swine feed.

Complete swine feed was prepared by mixing ground corn, soybean meal and other feed ingredients. The exact composition of the feed prepared in example 1 is indicated in below Table 1. A 2722-kilogram (2.722 metric ton) batch of feed was prepared in this manner.

TABLE 1

| PGF Diet Name | PGF WF4 (FALL) | |
|---|---|---|
| Ingredient | pounds | % |
| CORN (GROUND) | ≤994.60 | ≤49.73 |
| SOYBEAN MEAL | 513.00 | 25.65 |
| DISTILLERS | 400.00 | 20.00 |
| FAT | 29.00 | 1.45 |
| LYSINE HCL | 11.90 | 0.595 |
| DL-METHIONINE-99% | 3.20 | 0.16 |
| LIMESTONE | 18.50 | 0.925 |
| COPPER CHLORIDE | 0.70 | 0.035 |
| SALT | 12.00 | 0.60 |
| MONOCALCIUM PHOSPHATE 21% | 9.60 | 0.48 |
| L-THREONINE | 3.80 | 0.19 |
| L-TRYPTOPHAN | 0.70 | 0.035 |
| PGF VTM 3LB PHYTASE | 3.00 | 0.15 |
| Ingredient Total: | 2000.00 | 100.00 |

After the manufacture of the feed, the feed was delivered and placed into an on-farm feed storage bin. This feed would provide enough for 100 pigs during a period of 15 days. Once the feed bin had been filled, a 454-gram ice block that had previously been frozen, stored at −80° C. and contained three selected RNA viruses was dropped into the top of the feed bin on day 0. Because the ice block was dropped onto the top of the batch of feed, the ice block could naturally melt into liquid, enabling the three viruses to permeate the feed. Over the duration of the study (15 days), the permeated feed containing the three RNA viruses flowed to the bottom of the feed bin (via gravity) and was transferred into the pig barn through a plastic tube containing a flexible auger. Some additional mixing occurred as the feed was gradually transferred by the auger into the pig barn to provide the pigs with ad libitum consumption of the feed.

The three RNA viruses contained in the ice block were: Porcine Reproductive and Respiratory Syndrome virus (PRRSV 174), Porcine Epidemic Diarrhea virus (PEDV) and Seneca Virus A (SVA). Amongst those viruses, SVA is the only non-enveloped virus. PRRSV 174 and PEDV are enveloped viruses. SVA is sometimes chosen as a surrogate for foot-and-mouth disease virus (FMDV). FMDV is also a non-enveloped virus. Survival of enveloped viruses is usually different from survival of non-enveloped viruses.

The composition of the 454 g/454 mL ice block was as follows:

- 100 mL SVA (5 logs TCID50/mL, Ct=20.72), and
- 100 mL PRRSV 174 (5 logs TCID50/mL, Ct=21.38), and
- 100 mL PEDV (5 logs TCID50/mL, Ct=24.25),
- balanced with 154 mL serum free minimum essential media (MEM).

The indicated Ct values relate to PCR (polymerase chain reaction). It is generally accepted that Ct values of ≥38 are an indication for the absence of the respective virus. Thus, the measured Ct values from 20.72 to 24.5 confirm the presence of the respective virus.

Because the batch of feed delivered on day 0 was anticipated to last for the duration of the study (15 days), a second ice block containing the three viruses (identical to that used on day 0) was dropped on top of the feed remaining in the feed bin on day 6. This was done to ensure that remaining feed was also permeated with the three viruses as the second ice block melted and the feed gradually entered the pig barn via gravity flow into the contained auger system that provided the pigs with ad libitum consumption until day 15.

On day 6, individual swiffer cloths were drawn across each of the 6 feed troughs within the pig barn, contacting feed particles present where pigs consumed the feed. Afterwards, the cloths were immersed in sterile saline and a 3 mL aliquot was decanted for testing. Samples were evaluated for the presence of viral nucleic acid by PCR.

On day 15, individual swiffer cloths were used for testing again as described above. The results of the two PCR analysis are shown in Table 2. The notation “5/6” means that 6 individual samples were tested from 6 feed troughs within the pig barn, wherein 5 of the feed trough samples (i.e. feeder samples) out of the 6 contained RNA of the respective virus. The notations “6/6”, “4/6” and “3/6” are to be understood in the same manner.

TABLE 2

| | Feeder Samples | | |
|---|---|---|---|
| | PRRSV | PEDV | SVA |
| Day 6 | 5/6 | 5/6 | 3/6 |
| Day 15 | 6/6 | 6/6 | 4/6 |

Kinetics:

When an ice block is dropped onto the top of the feed inside of a feed bin, it gradually and naturally melts, allowing the liquid to permeate downward into the feed, starting in the upper portions of the feed. A typical feed storage bin, like those used in this study, is conical at the bottom so that the stored feed can naturally flow downward into a hopper where it is transferred by a flexible auger into the barn and deposited into any number of self-feeders with storage hoppers located within the pig pens. When feed in the outside storage bin is needed for the pigs being fed in the barn, feed is drawn into the auger from the bottom center of the bin. Generally, feed is drawn more quickly from the center of the bin and the feed nearest the outside perimeter of the bin tends to naturally flow more slowly and enter the barn later. Therefore, when an ice block is dropped onto to the top of the feed in the center of the bin and begins to melt, permeated feed is flowing into the auger and the pig barn more quickly than the rest of the feed. If the ice block is not completely melted when it reaches the auger, melting and dispersion of ice chunks is further accomplished by the mechanical action of the auger transferring the permeated feed into the barn. Thus, the mechanical action of the auger accomplishes further mixing and permeation as the feed is delivered into the barn. The self-contained auger passes through a wall of the barn (that is sealed around the auger) to deliver feed to the pigs. During winter (in Minnesota, U.S.A.), when an ice block will melt more slowly inside a feed bin, the warmer temperature sustained for the pigs inside the barn ensures that any remaining ice particles in the feed become completely melted as the feed passes through the auger to the self-feeders, so that the liquid has completely permeated the feed before it is consumed by the pigs. Permeating the feed with the viruses at cooler temperatures increases the likelihood of the viruses remaining infectious for a longer period of time. Dropping a second ice block onto the top of the feed remaining in the bin after 6 days ensures that the feed to be consumed in the following 9 days (up to day 15) is permeated in the same manner as the feed was during the first 6 days.

Interpretation of the Data Shown in Table 2:

Checking the presence of virus RNA in the feeder on day 6 and on day 15, respectively, is a test whether the intended virus RNA is successfully introduced into the feed and feed delivery system and might be viable for ingestion by the pigs. For all three viruses, different results were obtained for day 6 and day 15. Apparently, it is difficult to thoroughly contaminate the feed entering the barn during the first 6 days by simply dropping a single ice block in the center of the bin on day 0, but the feed becomes more thoroughly contaminated during the remaining 9 days after the addition of the second ice block on day 6. The results in Table 2 also suggest that the detection of non-enveloped SVA is challenging. Nevertheless, the presence of SVA in the batch of feed was beyond any doubt because, on day 15, all pigs showed clinical signs of SVA, regardless of the feed pan/pen from which they had been fed in the barn.

Example 2

In example 2, the test of example 1 was simultaneously replicated. In example 2, however, a mixture comprising benzoic acid flakes and a powder comprising thymol and eugenol was added and included with the feed composition shown in Table 1. Feed containing 0.312 weight-% of the mixture in substitution for an equal amount of ground corn, based on the total weight of the feed, was prepared.

Feeder samples were then taken as explained in example 1 on day 6 (i.e. 6 days after introduction of the first ice block into the feed) and on day 15 (i.e. 9 days after introduction of the second ice block). The different time spans, "day 0→day 6" and "day 6→day 15", are illustrated in the FIGURE. The results are shown below in Table 3.

The results in Table 3 show that a mixture comprising benzoic acid flakes and a powder comprising thymol and eugenol (0.312 weight-% in total, based on the total weight of the feed) is a very effective manner to reduce the presence of the three different kinds of viruses in feed (i.e. PRRSV, PEDV and SVA). In case of PRRSV and SVA, the treatment was more effective if the virus had been exposed to benzoic acid, thymol, and eugenol for a longer period of time (9 days beyond the initial 6 days). In the case of PEDV, there was no additional benefit to increasing the exposure time. In other words, the mixture of benzoic acid, thymol, and eugenol inactivates PEDV quickly.

Quick inactivation of the virus is beneficial because pig farmers prefer to not hold or quarantine feeds in storage before they are needed by the animals. Any need for a holding time, especially longer times, makes the life of a farmer more complicated and increases costs associated with storage and logistics for efficient pork production. Additionally, longer holding times can reduce the quality of the feed, as the stability and retention of some essential nutrients (i.e. vitamins) can be reduced over increased periods of time. On the other hand, farmers are very willing to accept and use holding times for feed if that will reduce the risk for spread of animal diseases, which may cause their animals to become sick and/or increase the likelihood for greater animal and economic losses within the entire pork industry.

TABLE 3

| virus | day of feeder sampling | duration of exposure of virus to mixture | positively tested samples vs. total number samples (example 2) | positively tested samples vs. total number samples (control; example 1) | Δ (effect of exposure to mixture during indicated duration) | assessment |
|---|---|---|---|---|---|---|
| PRRSV | Day 6 | 6 days | 2/6 | 5/6 | 3 fewer feeders tested positive | slightly longer duration of |
| | Day 15 | ≥9 days | 2/6 | 6/6 | 4 fewer feeders tested positive | treatment appears to be beneficial |
| SVA | Day 6 | 6 days | 3/6 | 3/6 | 0 (no effect in PCR test) | slightly longer duration of |
| | Day 15 | ≥9 days | 2/6 | 4/6 | 2 fewer feeders tested positive | treatment is beneficial |
| PEDV | Day 6 | 6 days | 1/6 | 5/6 | 4 fewer feeders tested positive | no need for increasing the |
| | Day 15 | ≥9 days | 2/6 | 6/6 | 4 fewer feeders tested positive | duration of the treatment; mixture appears to be fast-acting on PEDV |

*≥9 days may be any exposure from 9 days to 15 days; see section "Kinetics" above Example 3

In example 3, the effect of various concentrations of the mixture of example 2 (i.e. benzoic acid, thymol, and eugenol) in feed on the detection of three kinds of virus RNA in feeder samples on day 6 is elaborated. The two concentration that were tested are:

Low concentration: 0.312 weight-% of the mixture of example 2, based on the total weight of the feed.

High concentration: 0.52 weight-% of the mixture of example 2, based on the total weight of the feed.

In example 3, the test of example 2 was simultaneously replicated. For details about the test method, see example 2.

On day 6, feeder samples were then taken and analysed as described in the previous examples. The results are shown in Table 4, also including the results from examples 1 and 2).

TABLE 4

| | Feeder Samples on Day 6 | | |
|---|---|---|---|
| | PRRSV | PEDV | SVA |
| Control (example 1) | 5/6 | 5/6 | 3/6 |
| Low concentration (0.312 weight-%; example 2) | 2/6 | 1/6 | 3/6 |
| High concentration (0.52 weight-%; example 3) | 2/6 | 1/6 | 3/6 |

The results show that the mixture of benzoic acid, thymol, and eugenol was already effective at combating PRRSV, PEDV and SVA at the lower of the two concentrations. For these viruses, there is no need to increase the concentration of the mixture from 0.312 weight-% to 0.52 weight-%, based on the total weight of the feed. This is highly relevant for farmers because any need for higher amounts of a feed additive increases the cost.

Example 4

A synopsis of the results of examples 2 and 3 shows that the mixture of benzoic acid, thymol, and eugenol has outstanding performance against PEDV. More specifically, these examples show that the mixture of benzoic acid, thymol, and eugenol is effective against PEDV (i) after short time and (ii) at low concentration.

In some of the tested feed samples, RNA from PEDV could be detected by PCR despite of having added a mixture of benzoic acid, thymol, and eugenol to the respective feed. However, positive RNA results are not always indicative of the presence of viable virus. Positive RNA results in a PCR test may also be obtained in case of an inactivated virus (i.e. false positive result in PCR test). False positive results in PCR test can be revealed by looking at the corresponding animal data: animals cannot become sick by ingesting non-viable virus.

To confirm that 0.312 weight-% of the mixture, based on the total weight of the feed, sufficiently inactivates PEDV, the following was done:

measuring the mean growth rates (Average Daily Gain, ADG) of the pigs from day 0 to day 15 scoring the pigs for the presence of clinical symptoms (diarrhea as evidence for the disease) on day 15 testing the pigs for PEDV in rectal swab samples (as evidence for infection) collected on day 15

The results below in Table 5 show that any PEDV RNA detected by PCR in the feeder samples taken on day 6 and day 15 originated from inactivated and thus harmless PEDV.

TABLE 5

| | assessment on Day 15 concluding diagnostic, clinical, and growth results | | |
|---|---|---|---|
| | PEDV | | ADG, lb. |
| | infection (pig) | disease (pen) | day 0 to day 15 |
| Control (example 1) | 100% | 100% | 0.31 |
| Low concentration (0.312 weight-%; example 2) | 0% | 0% | 1.10 |
| High concentration (0.52 weight-%; example 3) | 0% | 0% | 1.19 |

Table 6 also confirms that pigs become infected by PEDV if an ice block containing PEDV is melted in feed that does not contain benzoic acid, thymol, and eugenol. Furthermore, Table 6 shows that for inactivating PEDV in feed, the lower concentration of the mixture of the invention is sufficient.

Example 5

In example 5, the impact of PRRSV and SVA on pigs that had been eating the feed with or without mixture was determined as explained in example 4. Table 6 shows the complete data, including the data from example 4:

TABLE 6

| | assessment on Day 15 concluding diagnostic, clinical, and growth results | | | | | | |
|---|---|---|---|---|---|---|---|
| | infection (pig)[1] | | | disease (pen)[2] | | | ADG, lb. |
| | PRRSV | PEDV | SVA | PRRSV | PEDV | SVA | day 0 to day 15 |
| Control (example 1) | 100% | 100% | 30% | 100% | 100% | 100% | 0.31 |
| Low concentration (0.312 weight -%; example 2) | 0% | 0% | 0% | 0% | 0% | 0% | 1.10 |
| High concentration (0.52 weight -%; example 3) | 0% | 0% | 0% | 0% | 0% | 0% | 1.19 |

[1] represented as percent of animals with virus recovered from biological samples (PRRSV = serum, PEDV = rectal swabs, or SVA = tonsil).
[2] represented as percent of pens demonstrating clinical signs of disease (dyspnea/weight loss/rough hair = PRRSV, diarrhea = PEDV, or lameness/vesicles = SVA).

The invention claimed is:

1. A method of making a porcine epidemic diarrhea virus (PEDV) inhibited swine animal feed mixture, wherein the method comprises:

(i) preparing a swine animal feed mixture by adding to a swine animal feed a PEDV-inhibiting effective amount of less than 0.5 weight-% of a PEDV-inhibiting mixture comprised of, based on the total weight of the swine animal feed:

(a) 0.25 to 0.475 weight-% of benzoic acid, and (b) a powder comprising 0.010 to 0.019 weight-% of a combination of eugenol and thymol, and (ii) allowing the PEDV-inhibiting mixture to degrade viral RNA from the PEDV in the swine animal feed mixture by storing the swine animal feed mixture prepared according to step (i), wherein the PEDV-inhibiting mixture is added in a sufficient amount such that the swine animal feed mixture exhibits Ct values as determined by real-time quantitative reverse transcriptase polymerase chain reaction of 38 or above for a holding time period of less than 7 days to form a PEDV inhibited swine animal feed mixture.

2. The method according to claim 1, comprising:

adding the benzoic acid in the form of benzoic acid flakes to the swine animal feed in an amount of 0.25 to 0.4 weight-%, based on the total weight of the swine animal feed, and/or adding the powder comprising eugenol and thymol in an amount from 0.010 to 0.019 weight-%, based on the total weight of the swine animal feed.

3. The method according to claim 2, which the benzoic acid flakes are added to the animal feed in an amount of 0.25 to 0.39 weight-% based on the total weight of the swine animal feed.

4. The method according to claim 1, wherein the powder comprises, based on the total weight of the powder, from 10 weight-% to 60 weight-% of auxiliary compounds and/or less than 5 weight-% of fully hydrogenated fat, partially hydrogenated fat or non-hydrogenated fat.

5. The method according to claim 4, wherein the powder comprises, based on the total weight of the powder, from 10 weight-% to 53 weight-% of the auxiliary compounds.

6. The method according to claim 4, wherein the powder comprises, based on the total weight of the powder, from 10 weight-% to 30 weight-% of the auxiliary compounds.

7. The method according to claim 1, wherein the swine animal feed mixtures exhibits the Ct values of 38 or above for a holding time period of less than 6 days.

8. The method according to claim 1, wherein the swine animal feed mixtures exhibits the Ct values of 38 or above for a holding time period of less than 5 days.

9. The method according to claim 1, wherein the swine animal feed mixtures exhibits the Ct values of 38 or above step for a holding time period of less than 3 days.

10. A method of inhibiting transmission of porcine epidemic diarrhea virus (PEDV) to a swine animal comprising:

(a) providing the PEDV-inhibited swine animal feed mixture made according to claim 1, and (b) feeding the PEDV-inhibited swine animal feed mixture to the swine animal.

* * * * *